United States Patent
Scholz et al.

(10) Patent No.: US 11,193,147 B2
(45) Date of Patent: Dec. 7, 2021

(54) ANTIMICROBIAL PRESERVATIVES FOR COSMETIC PRODUCTS

(71) Applicant: Active Micro Technologies, LLC, Lincolnton, NC (US)

(72) Inventors: Durant Scholz, Lincolnton, NC (US); Erica Segura, Denver, NC (US); Maureen Danaher, Charlotte, NC (US); Monica Beltran, Pineville, NC (US)

(73) Assignee: Active Micro Technologies, LLC, Lincolnton, NC (US)

( * ) Notice: Subject to any disclaimer, the term of this patent is extended or adjusted under 35 U.S.C. 154(b) by 303 days.

(21) Appl. No.: 16/538,138

(22) Filed: Aug. 12, 2019

(65) Prior Publication Data
US 2020/0048663 A1    Feb. 13, 2020

Related U.S. Application Data

(60) Provisional application No. 62/717,093, filed on Aug. 10, 2018.

(51) Int. Cl.
| | |
|---|---|
| *C12P 7/24* | (2006.01) |
| *A01N 31/04* | (2006.01) |
| *A61K 8/99* | (2017.01) |
| *A61K 8/9728* | (2017.01) |
| *A61Q 5/00* | (2006.01) |
| *C12P 7/22* | (2006.01) |
| *A61Q 19/10* | (2006.01) |
| *C12N 1/20* | (2006.01) |
| *C12N 1/16* | (2006.01) |
| *C12P 39/00* | (2006.01) |
| *A61Q 5/12* | (2006.01) |

(52) U.S. Cl.
CPC ............. *C12P 7/24* (2013.01); *A01N 31/04* (2013.01); *A61K 8/9728* (2017.08); *A61K 8/99* (2013.01); *A61Q 5/002* (2013.01); *A61Q 5/12* (2013.01); *A61Q 19/10* (2013.01); *C12N 1/16* (2013.01); *C12N 1/20* (2013.01); *C12P 7/22* (2013.01); *C12P 39/00* (2013.01)

(58) Field of Classification Search
None
See application file for complete search history.

(56) References Cited

FOREIGN PATENT DOCUMENTS

| | | | |
|---|---|---|---|
| EP | 2654432 A2 | 10/2013 | |
| WO | 2004098291 A2 | 11/2004 | |
| WO | 2012085255 A3 | 1/2013 | |

*Primary Examiner* — Robert J Yamasaki
(74) *Attorney, Agent, or Firm* — Lerner, David, Littenberg, Krumholz & Mentlik, LLP

(57) ABSTRACT

A method for producing an antimicrobial agent is provided. The method includes co-fermenting at least one bacterium and at least one yeast in a growth media to produce a co-fermented product. The co-fermented product includes an antimicrobial agent. A filtration method is applied to the co-fermented product to isolate and extract the antimicrobial agent from the co-fermented product, wherein the antimicrobial agent is a secondary metabolite.

12 Claims, 3 Drawing Sheets

ANTIMICROBIAL PRESERVATIVES FOR COSMETIC PRODUCTS

CROSS REFERENCE TO RELATED APPLICATIONS

The present application claims priority from U.S. Provisional Patent Application No. 62/717,093, the disclosure of which is incorporated by reference herein.

FIELD OF THE INVENTION

The present invention relates to generation of antimicrobial agents, and more specifically, to use of these antimicrobial agents to maintain the microbiological safety of cosmetic and personal care products by reducing the amount of microbial contaminants, in turn, reducing or inhibiting fungal and/or bacterial growth.

BACKGROUND INFORMATION

Recently, enhanced product safety regulations have driven consumers to select natural cosmetic and personal care products. However, as consumer use of these products increases, the likelihood of microbial and fungal growth and contamination within containers housing these products also increases. Of specific concern is the headspace area of the package, or the space between the product (housed within the container) and the lid of the container. Headspace area preservation becomes an issue when the container does not adequately protect the product from fungal or mold contamination, which may result from the manufacturing environment, poor storage conditions, or consumer use. For example, microbial or fungal growth may occur in this headspace area when a hot substance is poured into the container and subsequently cools. Alternatively or additionally, microbial growth may occur each time a consumer opens and uses the product, as the headspace area becomes exposed to the air and to the contaminants within the air.

The current solution to this problem includes use of preservatives as antimicrobials to maintain the microbiological safety of cosmetic and personal care products. Examples of these preservatives may include: parabens (e.g., germaben II, methylparben, propylparaben, and butylparaben), formaldehyde releasers (e.g., germall plus, DMDM hydantoin, imadozolidinyl urea, and diazolidinyl urea), Isothiazolinones (e.g., kathon), phenoxyethanol (e.g., optiphen and optiphen plus), and organic acids (e.g., benzoic acid/sodium benzoate, sorbic acid/potassium sorbate, levulinic acid, and anisic acid). However, some of these preservatives, such as the isothiazolinone and phenoxyethanol, may cause skin and lung irritation and/or toxicity to the kidneys, nervous system, and/or liver.

Therefore, there is a need for a natural, safe, and non-irritating product to reduce or eliminate microbial contaminants within the headspace area of a container housing a cosmetic or personal care product.

SUMMARY OF THE INVENTION

This present invention addresses this problem by providing an antimicrobial agent, and an associated method for generating the antimicrobial agent, which is configured to prevent or inhibit fungal growth within an area of a closed container housing a product. In some embodiments, the method may include generating an antimicrobial agent by co-fermenting at least one bacterium and at least one yeast in a growth media, and applying one or more filtration methods to the co-fermented product to isolate and extract secondary metabolites from the co-fermented product for use as the antimicrobial agent.

A method for producing an antimicrobial agent, including co-fermenting at least one bacterium and at least one yeast in a growth media to produce a co-fermented product. The co-fermented product includes an antimicrobial agent. A filtration method is applied to the co-fermented product to isolate and extract the antimicrobial agent from the co-fermented product, wherein the antimicrobial agent is a secondary metabolite.

The secondary metabolite of the antimicrobial agent may be cinnamic aldehyde, phenylethyl alcohol, and combinations thereof. The at least one bacterium of the co-fermentation may be *Bacillus subtilis* and at least one yeast may be *Saccharomyces boulardii*. The growth media of the co-fermentation may be ammonium sulfate, magnesium sulfate, disodium phosphate, yeast autolysate, and combinations thereof.

The co-fermentation is performed at a temperature in a range of about 18° C. to about 22° C., preferably at a temperature of about 20° C. The co-fermentation is performed for a time period in a range of about 12 hours to about 18 hours at a pH in a range of about 4.0 to about 6.2, preferably at a pH in a range of about 5.8 to about 6.2.

A packaged product having a container having a body and a lid. The body having an inner volume and an opening that is fluidly coupled to the inner volume. The lid having a first side and an opposing second side, wherein the first side of the lid is configured to contact the opening when the container is in a closed position. A product is disposed in the inner volume, wherein the product includes a composition and an antimicrobial agent.

In the packaged product, a portion of the inner volume is unoccupied by the product. The portion unoccupied by the product is located between the product and the first side of the lid when the container is in the closed position.

The composition of the product may be a gel, a cream, a lotion, a liquid, and a powder. The antimicrobial agent prevents or inhibits fungal growth from fungi, the fungi may be *Penicillium brevicompactum, Fusarium* sp, and combinations thereof.

The container may include a material of a natural polymeric material, a synthetic polymeric material, and combinations thereof.

The antimicrobial agent of the product may include secondary metabolites extracted from a co-fermented byproduct of at least one bacterium and at least one yeast in a growth media, where the at least on bacterium includes *Bacillus subtilis* and the at least one yeast includes *Saccharomyces boulardii*. The antimicrobial agent of the product may include cinnamic aldehyde, phenylethyl alcohol, and combinations thereof.

An antimicrobial agent is prepared by co-fermenting at least one bacterium and at least one yeast in a growth media to form a co-fermented product containing the antimicrobial agent, and isolating and extracting the antimicrobial agent from the co-fermented product. The antimicrobial agent may include a secondary metabolite, wherein the secondary metabolite may be cinnamic aldehyde, phenylethyl alcohol, and combinations thereof.

A cosmetic or personal care product including the antimicrobial agent prepared by co-fermenting at least one bacterium and at least one yeast in a growth media.

BRIEF DESCRIPTION OF THE DRAWINGS

This invention may be best understood by reference to the following description taken in conjunction with the accompanying drawing figures in which.

DETAILED DESCRIPTION

The present invention provides antimicrobial agents for use in the prevention and inhibition of microbial growth within an area of a closed container that houses a product and an associated method for generating the antimicrobial agent. It should be appreciated that the antimicrobial agent may be formed naturally or synthetically.

Figure 1:
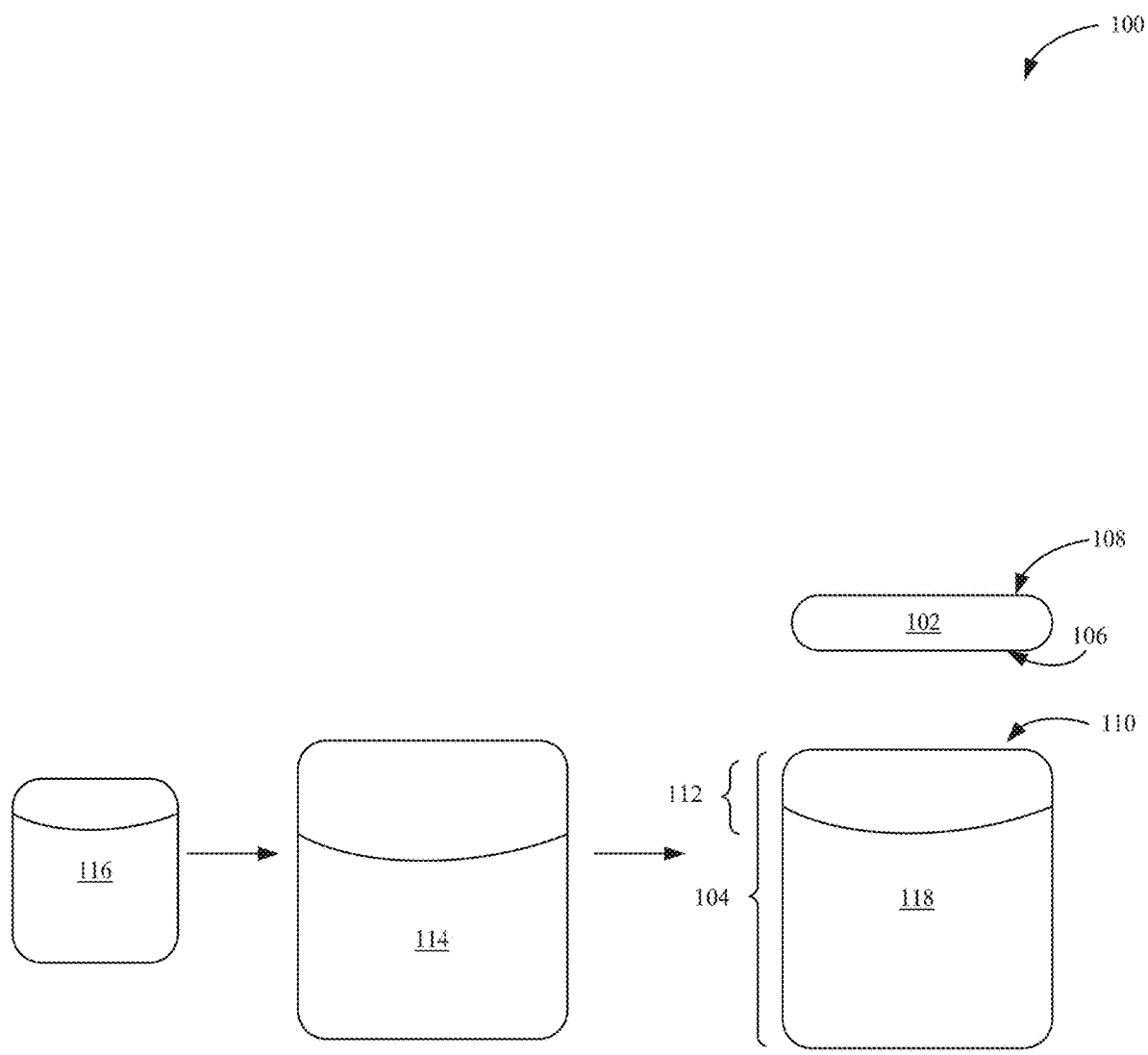
FIG. 1 depicts a schematic diagram involving combining an antimicrobial agent and a composition housed within a container to prevent or inhibit fungal growth within the container, according to at least some embodiments disclosed herein.

FIG. 1 depicts a schematic diagram involving combining an antimicrobial agent and a composition in a container to prevent or inhibit fungal growth within the container, according to at least some embodiments disclosed herein.

FIG. 1 depicts schematic diagram of a container assembly 100. The container assembly may include lid 102 and body 104. According to some embodiments, the container assembly may be made of a material including a natural polymeric material and/or a synthetic polymeric material. Lid 102 may include first side 106 opposing second side 108. Body 104 of the container assembly may include opening 110. Antimicrobial agent 116 may be combined with composition 114 to form product 118 via any method known by those having skill in the art. Composition 114 may reside within body 104 of the container assembly before being combined with antimicrobial agent 116. In some embodiments, the composition 114 may be a cosmetic product or personal care product. In some embodiments, the composition 114 may be in the form of a gel, a cream, a lotion, a liquid, or a powder, among other embodiments known to those of skill in the art. It should be appreciated that the form of antimicrobial agents and any compositions exemplified are not limited to the examples provided herein and other forms of product 118 are contemplated.

Antimicrobial agent 116 may prevent or inhibit microbial growth within another area of the closed container assembly. In some embodiments, the microbial growth may include fungal growth from *Penicillium brevicompactum* species and/or any species of the genus *Fusarium*. The other area may include headspace area 112, or an area between product 118 and first side 106 of lid 102.

Antimicrobial agent 116 may be generated by co-fermenting a bacterium and a yeast in a growth media. In some embodiments, the co-fermentation process may include a bio-fermentation process. In some embodiments, the bacterium may be selected from *Bacillus subtilis* cells, the yeast may be selected from *Saccharomyces boulardii*, and the growth media may be selected from: ammonium sulfate, magnesium sulfate, yeast autolysate, and combinations thereof. It should be appreciated that the bacterium, the yeast, and the growth media are not limited to the examples described herein and other examples are contemplated. In some embodiments, at the beginning of the co-fermentation process, the amount of bacterium and yeast added is about 10% to about 20% of the total composition of the bacterium, yeast and growth media. In some embodiments, the amount of growth media added is about 80% to about 90% of the total composition of the bacterium, yeast and growth media. In some embodiments, the co-fermentation process may include $1.15 \times 10^9$ of bacterium and $0.15 \times 10^9$ of yeast. The co-fermentation process may be maintained at a temperature in a range of about 18° C. to about 22° C. and may occur for a time period in a range of about 12 hours to about 18 hours. The co-fermentation process may be maintained at a pH in a range of about 4.0 to about 6.2. In some embodiments, the co-fermentation process may be maintained at a pH in a range of about 5.8 to about 6.2.

Subsequent to the co-fermentation process, one or more filtration methods may be applied to the co-fermented product to isolate and extract secondary metabolites from the co-fermented product for use as the antimicrobial agent. In some embodiments, at least one filtration method may include a solvent separation method. In some embodiments, the solvent may be 1,3-propanediol. The secondary metabolites may include volatile and organic metabolites configured to prevent or reduce diseases caused by antimicrobials by: (a) limiting ascospore and mycelium production, (b) inhibiting metabolism function, and/or (c) lysing mold cells. In some embodiments, the secondary metabolites may include cinnamic aldehyde, phenylethyl alcohol, and combinations thereof.

Figure 2:
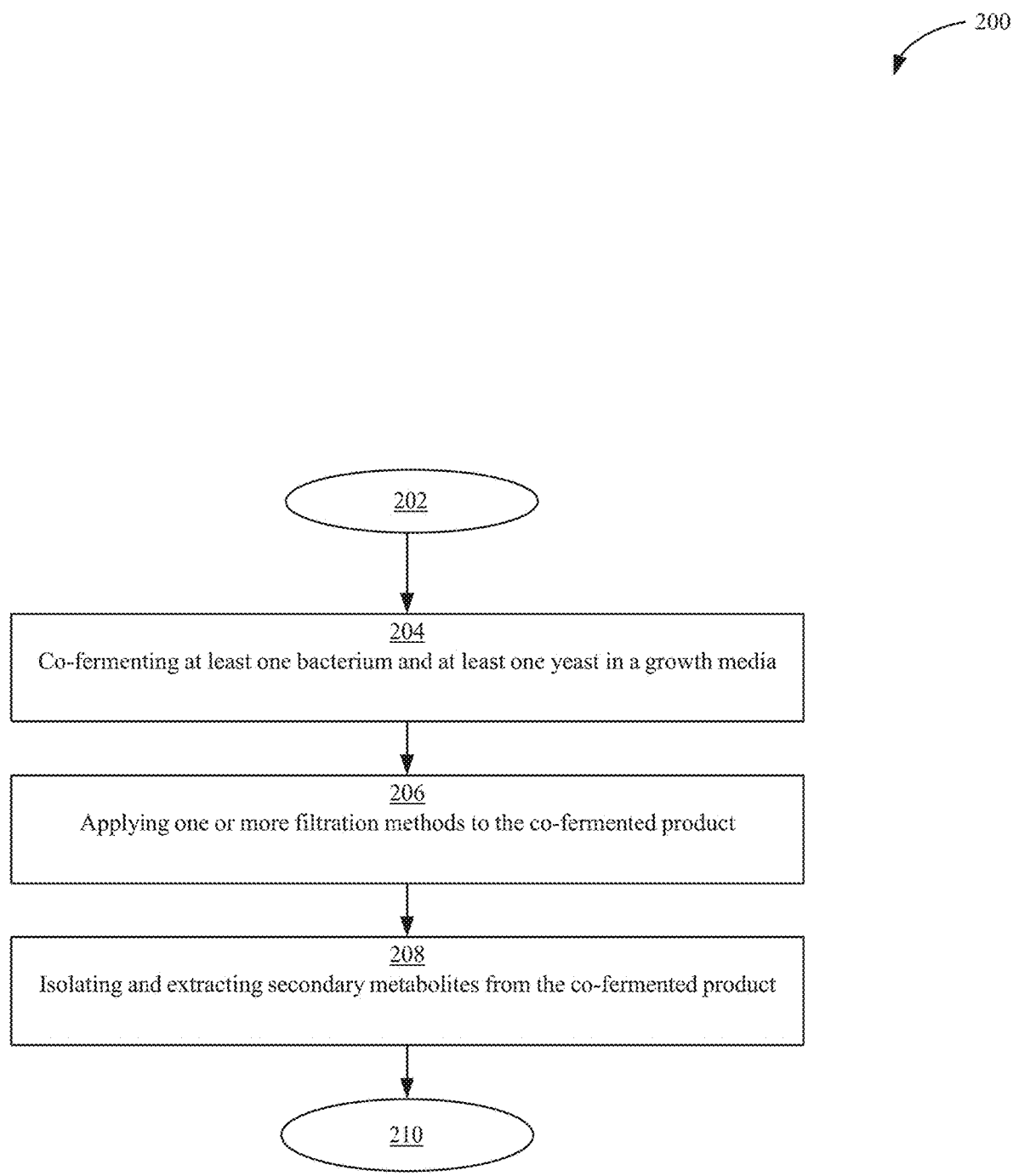
FIG. 2 depicts a flowchart associated with a method to generate an antimicrobial agent suitable for preventing or inhibiting microbial growth inside of a closed container, according to at least some embodiments disclosed herein.

FIG. 2 depicts a flowchart for a method 200 to generate an antimicrobial agent suitable for preventing or inhibiting microbial growth inside of a closed container according to at least some embodiments disclosed herein.

At step 202, the raw materials are checked for microbial contamination and that the raw materials are similar to previous batches by comparing the appearance, consistency and odor with retained samples before generating the antimicrobial agent. The Certificate of Analysis of the raw materials is also checked to match those of previous batches. Any liquid raw material is compared on an infrared (IR) spectrophotometer to previous batches.

At step 204, an antimicrobial agent is generated by co-fermenting at least one bacterium and at least one yeast in a growth media. In some embodiments, the at least one bacterium may include *Bacillus subtilis* cells and the at least one yeast may include *Saccharomyces boulardii*. In some embodiments, the growth media may include ammonium sulfate, magnesium sulfate, disodium phosphate, yeast autolysate, and combinations thereof. In some embodiments, the co-fermentation process may occur at a temperature in a range of about 18° C. to about 22° C., at a pH in a range of about 4.0 to about 6.2, and for a time period of about 12 hours to about 18 hours. In some embodiments, the co-fermentation process may occur at a temperature in a range of about 18° C. to about 22° C., at a pH in a range of about 5.8 to about 6.2, and for a time period of about 12 hours to about 18 hours, wherein the culture can achieve early stationary phase.

At step 206, one or more filtration methods may be applied to the co-fermented product. In some embodiments, the one or more filtration methods may include a solvent separation method. In some examples, a solvent, such as, 1,3-propanediol may be used. In operation, the co-fermented product may be mixed with the solvent to dissolve components of the co-fermented product, such as secondary metabolites, that it is desired to recover.

At step 208, the components of the co-fermented product, such as secondary metabolites, are isolated and extracted from the co-fermented product and used as an antimicrobial agent. In some examples, the secondary metabolites may include cinnamic aldehyde, phenylethyl alcohol, and combinations thereof.

At Step 210, quality control can be performed to conclude the process. Quality control can include checking for the presence of microorganisms under a microscope, appearance, color, odor, pH, and/or refractive index. During initial startup of batch production, samples can be obtained to determine heavy metal contents, such as lead, arsenic, and cadmium. In the case that quality control fails, changes can be made to the process. For example, an initial step may be refiltration and reexamination by quality control.

The flowchart of FIG. 2 illustrates architecture, functionality, and operation of possible implementations of systems and methods according to various embodiments of the present invention. In this regard, each block in the flowchart may represent a module, segment, or portion of instructions. In some alternative implementations, the functions noted in the blocks may occur out of the order noted in FIG. 2. For example, two blocks shown in succession may, in fact, be executed substantially concurrently, or the blocks may sometimes be executed in the reverse order, depending upon the functionality involved.

The antimicrobial agent suitable for preventing or inhibiting microbial growth may also improve moisture levels of the product when used. Thus, using a product including the antimicrobial agent of the present applicant shows high moisturizing capabilities.

EXAMPLES

Example 1: Preservation Efficacy Test (PET) Using the Antimicrobial Agent

An inoculum suspension was prepared by: using a sterile pipette to add about 9 ml of a buffered sodium chloride peptone solution (of a pH of about 7) to test tubes and autoclaving at about 121° C. for a time period of about 20 minutes. After sterilization was complete, a sterile piece of cotton was used to swab and add *Penicillium brevicompactum* and *Fusarium* sp. to a test tube with the sterile buffered sodium chloride peptone solution. The inoculum suspension included a minimum microbial population of about $10^6$ colony forming unit (CFU)/ml. Serial dilutions were then made in a ratio of 1:10 to achieve the microbial concentration using the buffered sodium chloride peptone solution. Further, the initial inoculum suspensions were plated per duplicate, using Sabouraud Dextrose Agar (SDA), to quantify the population after exposure in the test material for a specific time period.

The PET may be used to simulate contamination through inoculations containing micro-organisms over a period of time and then assessing the ability of preservatives to reduce or eliminate these micro-organisms. In the PET of Example 1 the inventive antimicrobial agent, another antimicrobial agent as a positive control, and no antimicrobial agent as a negative control were accessed for reduction in bacteria growth.

A base cream was poured into three containers at a temperature of about 45° C. The containers are each a 1 ounce white polypropylene double-wall radius jar. The base cream filled about 75 Vol % of each container, with about 25 Vol % of each container remaining empty and constituting the headspace area.

An antimicrobial agent ("co-fermented antimicrobial agent", 1 Vol %) was combined with the base cream and then added to container 1. This antimicrobial agent was generated by co-fermenting *Bacillus subtilis* and *Saccharomyces boulardii* in a growth media.

An antimicrobial agent ("bacteria-fermented antimicrobial agent", 1 Vol %) generated by fermenting *Bacillus subtilis* was combined with the base cream in container 2. Container 2 serves as a positive control.

No antimicrobial agent was added to the base cream in container 3. Container 3 serves as a negative control. In this case, the base cream of container 3 is considered 'unpreserved'.

The *Penicillium brevicompactum* and the *Fusarium* sp. (prepared in Example 1) were isolated via a passive sedimentation method and were added in units of $10^6$ CFU/ml to the lid of each container separately. Each lid (or cap) was closed and each of the containers were stored at a temperature in a range of about 23° C. to about 25° C. A sterile swab of the buffered sodium chloride peptone solution was utilized to take a sample from each cap. Each cap was tested at various days, measured from the initial inoculation, including at day 7, day 14, day 21, and day 28 to determine the preservation efficacy of headspace in the container. The preservation efficacy of headspace is presented below in Table 1.

TABLE 1

Results of PET using the Antimicrobial Agent

| Test Product | Testing Day | *Penicillium brevicompactum* | *Fusarium* sp. |
|---|---|---|---|
| Base cream combined with antimicrobial agent generated by co-fermenting a bacterium and a yeast | Day 7 | No Growth | No Growth |
| | Day 14 | No Growth | No Growth |
| | Day 21 | No Growth | No Growth |
| | Day 28 | No Growth | No Growth |
| Base cream combined with antimicrobial agent generated by fermenting a bacterium | Day 7 | Growth | Growth |
| | Day 14 | Growth | Growth |
| | Day 21 | Growth | Growth |
| | Day 28 | Growth | Growth |
| Unpreserved base cream (no antimicrobial agent) | Day 7 | Growth | Growth |
| | Day 14 | Growth | Growth |
| | Day 21 | Growth | Growth |
| | Day 28 | Growth | Growth |

In Table 1, the *Penicillium brevicompactum* column and *Fusarium* sp. column display the reduction in microbial growth under the associated conditions. "Growth" indicates a reduction of the micro-organisms by less than 99.999% or that at least 1 bacteria colony was observed. "No Growth" may indicate a reduction of the micro-organisms by more than 99.999% or that no bacteria colonies were observed. For example, the co-fermented antimicrobial agent in combination with the base cream in container 1 exhibited "No Growth" of either *Penicillium brevicompactum* or *Fusarium* sp on any of the days measured. In contrast, the bacteria-fermented antimicrobial agent in combination with the base cream in container 2 and the unpreserved base cream of container 3 exhibited "Growth" on every day measured.

Example 2: PET of Different Cosmetic and Personal Care Products

PETs were performed on different cosmetic and personal care products for the co-fermented antimicrobial agent in comparison to the unpreserved product. The test methods, co-fermented antimicrobial agent, and conditions were the same as those in Example 1, with the exception that different cosmetic and personal care products were used in place of the base cream. The cosmetic products tested were a Split End Masque Formula, Renewing Body Scrub Formula, Exfoliating Face Mask Formula and Beard Balm Formula. As shown in Tables 2 to 5 below, the co-fermented antimicrobial agent again exhibited "No Growth" in each product over the test period.

TABLE 2

Results of PET of Split End Masque

| Test Product | Testing Day | *Penicillium brevicompactum* | *Fusarium* sp. |
|---|---|---|---|
| Split End Masque Formula with antimicrobial agent generated by co-fermenting a bacterium and a yeast | Day 7 | No Growth | No Growth |
| | Day 14 | No Growth | No Growth |
| | Day 21 | No Growth | No Growth |
| | Day 28 | No Growth | No Growth |
| Unpreserved Split End Masque Formula | Day 7 | Growth | Growth |
| | Day 14 | Growth | Growth |
| | Day 21 | Growth | Growth |
| | Day 28 | Growth | Growth |

TABLE 3

Results of PET of Renewing Body Scrub Formula

| Test Product | Testing Day | *Penicillium brevicompactum* | *Fusarium* sp. |
|---|---|---|---|
| Renewed Body Scrub Formula with antimicrobial agent generated by co-fermenting a bacterium and a yeast | Day 7 | No Growth | No Growth |
| | Day 14 | No Growth | No Growth |
| | Day 21 | No Growth | No Growth |
| | Day 28 | No Growth | No Growth |
| Unpreserved Renewed Body Scrub Formula | Day 7 | Growth | Growth |
| | Day 14 | Growth | Growth |
| | Day 21 | Growth | Growth |
| | Day 28 | Growth | Growth |

TABLE 4

Results of PET of Exfoliating Face Mask Formula

| Test Product | Testing Day | *Penicillium brevicompactum* | *Fusarium* sp. |
|---|---|---|---|
| Exfoliating Face Mask Formula with antimicrobial agent generated by co-fermenting a bacterium and a yeast | Day 7 | No Growth | No Growth |
| | Day 14 | No Growth | No Growth |
| | Day 21 | No Growth | No Growth |
| | Day 28 | No Growth | No Growth |
| Unpreserved Exfoliating Face Mask Formula | Day 7 | Growth | Growth |
| | Day 14 | Growth | Growth |
| | Day 21 | Growth | Growth |
| | Day 28 | Growth | Growth |

TABLE 5

Results of PET of Beard Balm Formula

| Test Product | Testing Day | *Penicillium brevicompactum* | *Fusarium* sp. |
|---|---|---|---|
| Beard Balm Formula with antimicrobial agent generated by co-fermenting a bacterium and a yeast | Day 7 | No Growth | No Growth |
| | Day 14 | No Growth | No Growth |
| | Day 21 | No Growth | No Growth |
| | Day 28 | No Growth | No Growth |
| Unpreserved Beard Balm Formula | Day 7 | Growth | Growth |
| | Day 14 | Growth | Growth |
| | Day 21 | Growth | Growth |
| | Day 28 | Growth | Growth |

Example 4: Moisturization Assay

An in-vivo study was conducted over a four week period to evaluate the moisturization benefits of the co-fermented antimicrobial agent in a base lotion in comparison to a base lotion and an untreated control. Ten subjects participated in the study. The subjects included both male and female subjects between the ages of 23 to 45. Each subject who participated were known to be free of any skin pathologies before participating in the study. To measure the moisture levels of the subject's skin, a Dermalab Comeometer was used, which measures the amount of water within the skin. The presence of moisture, or water, in the skin improvise conductance and results in a higher reader than dry skin. Thus, the higher the levels of moisture, the higher the readings from the Dermalab Comeometer will be.

Baseline moisturization readings were taken on day of the study for each subject. After the initial measurements, each subject was asked to apply 2 mg of each test material to their volar forearms. As a baseline, an untreated area of the volar forearm was also measured to compare the moisturization levels. The test materials included the co-fermented antimicrobial agent combined with the base lotion and only the base lotion.

Figure 3:
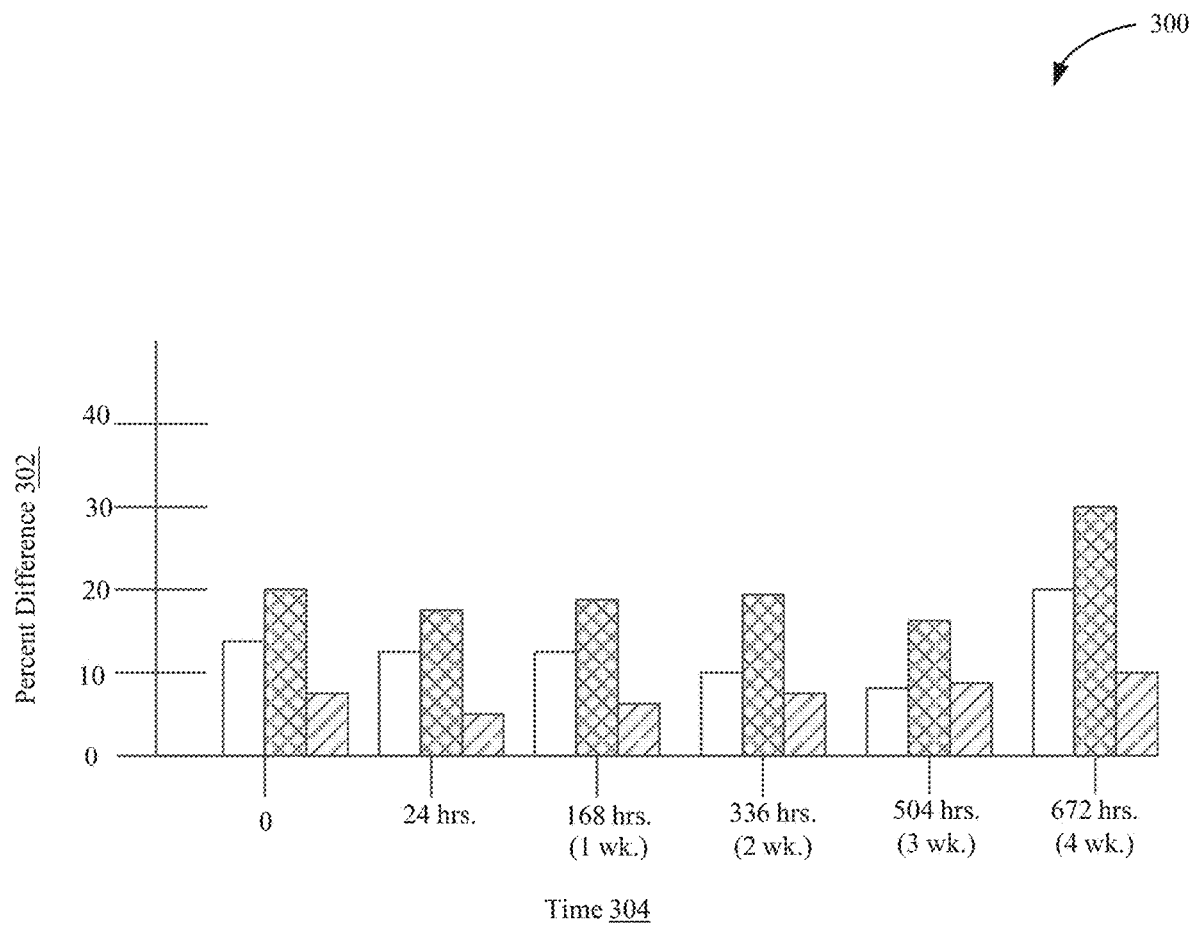
FIG. 3 depicts graphical results of a moisturization assay involving several antimicrobial agents located within a closed container, according to at least some embodiments disclosed herein.
Figure 3:
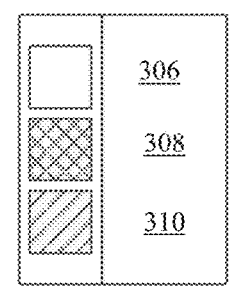

FIG. 3 depicts graphical results 300 of the moisturization assay, depicting x-axis 304 measuring time in hours and y-axis 302 measuring a percentage difference with respect to moisturization for each of a first comparison 306, second comparison 308, and third comparison 310.

The first comparison 306 is a comparison between the base lotion and the untreated control, e.g., the skin of a subject that received neither base lotion, nor the co-fermented antimicrobial agent combined with the base lotion. Second comparison 308 is a comparison between the co-fermented antimicrobial agent combined with base lotion and the untreated control. The third comparison 310 is a comparison between the co-fermented antimicrobial agent combined with base lotion and the base lotion. As shown in FIG. 3, the addition of co-fermented antimicrobial agent to the base lotion improve moisturization levels by about 16.5% after a 24 hour time frame and may improve moisturization levels by about 34% after a four week time frame, as compared to the untreated control. The addition of co-fermented antimicrobial agent to the base lotion may improve moisturization levels by about 9.88% after a four week time frame, as compared to the base lotion.

Table 6 below represents the average moisturization levels of the subjects. In Table 6, the first test material of the co-fermented antimicrobial agent combined with the base lotion showed higher moisturization capabilities than the other sites.

TABLE 6

| Averages | T = 0 | T = 24 Hours | T = 1 Week | T = 2 Weeks | T = 3 Weeks | T = 4 Weeks |
|---|---|---|---|---|---|---|
| Base Lotion combined with antimicrobial agent | 76.8 | 93.9 | 97.2 | 92.2 | 98.8 | 93.4 |
| Base Lotion | 72.2 | 90.3 | 92.8 | 86 | 91.9 | 85 |
| Untreated Site | 63.6 | 80.6 | 82.7 | 77.4 | 85.6 | 69.7 |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for producing an antimicrobial agent, comprising:
co-fermenting at least one bacterium comprising *Bacillus subtilis* and at least one yeast comprising *Saccharomyces boulardii* in a growth media to produce a co-fermented product, the co-fermented product including an antimicrobial agent; and
applying a filtration method to the co-fermented product to isolate and extract the antimicrobial agent from the co-fermented product, wherein the antimicrobial agent is a secondary metabolite selected from the group consisting of cinnamic aldehyde, phenylethyl alcohol, and combinations thereof.

2. The method of claim 1, wherein the filtration method comprises:
mixing the co-fermented product with a solvent; and
extracting the antimicrobial agent from the co-fermented product.

3. The method of claim 2, wherein extracting the antimicrobial agent further comprises:
dissolving the antimicrobial agent in the solvent to form a solution; and
filtering the solution having the dissolved antimicrobial agent from the remainder of the co-fermented product.

4. The method of claim 3, wherein the solvent comprises 1,3-propanediol.

5. The method of claim 1, wherein the growth media is selected from the group consisting of ammonium sulfate, magnesium sulfate, disodium phosphate, yeast autolysate, and combinations thereof.

6. The method of claim 1, wherein the co-fermenting step is performed at a temperature in a range of about 18° C. to about 22° C.

7. The method of claim 6, wherein the co-fermenting step is performed at the temperature of about 20° C.

8. The method of claim 1, wherein the co-fermenting step is performed for a time period in a range of about 12 hours to about 18 hours.

9. The method of claim 1, wherein the co-fermenting step is performed at a pH in a range of about 4.0 to about 6.2.

10. The method of claim 1, wherein the co-fermenting step is performed at a pH in a range of about 5.8 to about 6.2.

11. The method of claim 1, wherein, in the co-fermenting step, the at least one bacterium and the at least one yeast are present in a total amount of about 10% to about 20%, relative to the total amount of the at least one bacterium, the at least one yeast and the growth media.

12. The method of claim 1, wherein, in the co-fermenting step, the growth media is present in an amount of about 80% to about 90%, relative to the total amount of the at least one bacterium, the at least one yeast and the growth media.

* * * * *